(12) United States Patent
Trainoff

(10) Patent No.: US 6,452,672 B1
(45) Date of Patent: Sep. 17, 2002

(54) SELF CLEANING OPTICAL FLOW CELL

(75) Inventor: Steven P. Trainoff, Goleta, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 09/523,003

(22) Filed: Mar. 10, 2000

(51) Int. Cl.$^7$ ................................................ G01N 1/10
(52) U.S. Cl. ...................... 356/246; 356/244; 137/237
(58) Field of Search ................. 356/246, 244; 137/237

(56) References Cited

U.S. PATENT DOCUMENTS

| | | | |
|---|---|---|---|
| 4,165,179 A | * | 8/1979 | Sato ............................ 356/246 |
| 5,404,217 A | | 4/1995 | Janik |
| 5,656,095 A | | 8/1997 | Honda |
| 5,889,209 A | | 3/1999 | Piedrahita |
| 6,330,831 B1 | * | 12/2001 | Lynnworth et al. ...... 73/861.28 |

FOREIGN PATENT DOCUMENTS

| | | |
|---|---|---|
| CH | 636 200 | 5/1983 |
| DE | 197 48 725 A1 | 6/1999 |
| GB | 1 604 691 | 12/1981 |

OTHER PUBLICATIONS

Anonymous: "Disk and plate ultrasonic transducers", Internet Article.
Anonymous: "Ultraesonic products", Internet Article.
Branson Precision Processing: "Microcoustic small particle removal system series 9500", Internet Article, Mar. 9, 20000.

* cited by examiner

*Primary Examiner*—Frank G. Font
*Assistant Examiner*—Roy M. Punnoose
(74) *Attorney, Agent, or Firm*—Philip J. Wyatt

(57) ABSTRACT

Optical flow cells used, for example, for making scattered light measurements on liquid borne samples, are often affected by particulate materials that adhere to the internal optical surfaces. These contaminating particulates can cause distortions of the scattered light signals to be measured from the illuminated samples within the flow cell. Such particulates are difficult to remove, especially while the cell is assembled. A method for dislodging and removing such particulate contaminants is described that consists of attaching externally to the flow cell an ultrasonic generator whose frequency of operation may be tuned to couple most effectively with the internal structures of the flow cell itself. Such ultrasonic coupling must be accompanied by an impressed flow through the cell that can remove from the cell particulates that have been dislodged. In order to assure good mechanical action, the impressed ultrasonic frequency is swept over a range of frequencies.

18 Claims, 3 Drawing Sheets

SELF CLEANING OPTICAL FLOW CELL

PRIOR RELATED PATENTS AND APPLICATIONS

The present invention is directed to an optical flow cell design that can be cleaned automatically without invasive physical means. It is particularly useful when optical measurements are made following chromatographic separation since these are often associated with particulate material and air bubbles which tend to adhere to the optical surfaces themselves.

Expressly incorporated herein are the following patents and applications concerning flow cells and related structures whose performance would be improved with the new invention.

- U.S. Pat. No. 4,616,927—"Sample Cell for Light Scattering Measurements," (Oct. 14, 1996)
- U.S. Pat. No. 4,907,884—"Sample Cell Monitoring System," (Mar. 13, 1990)
- U.S. Pat. No. 5,305,071—"Differential Refractometer" (Apr. 19, 1994)
- U.S. Pat. No. 5,404,217—"Laser Liquid Flow Cell Manifold System and Method for Assembly," (Apr. 4, 1995)
- U.S. Pat. No. 5,530,540—"Light Scattering Measurement Cell for Very Small Volumes," (Jun. 25, 1996)
- Application Ser. No. 08/989,364 "A New Electrode Design for Electrical Field Flow Fractionation", Steven P. Trainoff. (Filed Dec. 12, 1997)
- Application Ser. No. 08/870,937 "Extended range interferometric refractometer", Steven P. Trainoff, David T. Phillips, Gary R. Janik, and Douglas W. Shepard. (Filed Jun. 6, 1997)

BACKGROUND

In the field of light scattering, as applied to determine the molar mass and mean square radius of solvated molecules, measurements are made from solutions comprised of a solvent containing a dissolved sample. By measuring the scattered light variation with scattering angle and measuring the concentration of the solute, one may in principle determine the molar mass and mean square radius of such solvated molecules. Similarly, the light scattering properties of sub micrometer particles in liquid suspension may be used to determine their average size. Light scattering techniques may be applied as well for measurements involving inelastic light scattering such as photon correlation spectroscopy, Raman spectroscopy, fluorescence, etc. These measurements, usually performed at a fixed single angle, are used to determine the hydrodynamic size of the particles or molecules illuminated.

Light scattering measurements are often made with a light scattering photometer wherein the sample is introduced into an optical cell such as referenced above in U.S. Pat. Nos. 4,616,927 and 5,404,217. Interfering with such optical measurements are a variety of contaminants whose presence inside the flow cell often contribute to the recorded light scattering signals in such a manner as to distort or even mask them. Such contaminants arise from various sources, many of which cannot be avoided. Included among these are small air bubbles, fine particles shedding from chromatographic columns if such are being employed to separate the molecules or sub-micrometer particles prior to measurement, aggregates formed from the sample itself which may have a strong affinity for the internal optical surfaces, contaminants in the poorly prepared solvent, debris from previous measurements that build up on the optical surfaces, etc.

During the measurement process, the presence of these contaminants are often recognized indirectly through the effects they have on the scattering or are noticeably visible through physical examination of the scattering cell, or both. There are various means by which such contaminants are removed or dislodged from the internal optical surfaces such as flushing the optical cell with different solvents such as acids or detergents or introducing a large air bubble in the manner of the familiar Technicon AutoAnalyzer of the 1960s. Sometimes, no matter how much effort has been expended, the flow cell must be disassembled and each component cleaned manually. Once disassembled, one of the most useful means for cleaning surfaces is to use ultrasonic waves as created in an ultrasonic cleaning bath. The components are placed in a fluid such as water and ultrasonic waves whose fixed frequencies are of the order 50 kHz are propagated throughout the bath. These waves are generally generated by means of piezoelectric transducers well coupled to the bath chamber. At the frequencies and power levels traditionally applied, cavitation effects generally cause the generation of bubbles which, when driven against a surface, tend to assist in the cleaning and scrubbing of such surfaces.

Although the disassembly of an optical cell and the subsequent cleaning of its parts in an ultrasonic bath are effected, it is time consuming. Unfortunately, it is often the only means possible. When the optical cell is used in a high temperature environment, such as is the case for chromatographic separations requiring high temperature solvents, the traditional disassembly concept becomes even more time-consuming since the temperature of the chromatograph itself must often be reduced significantly to obtain access to the optical cell which is then removed and cleaned. High temperature chromatographs, and especially the columns used therein, can be damaged during temperature cycling which, therefore, must be carefully executed. The process of cleaning an internally mounted optical cell can, in such a case, require up to 24 hours to effect a removal, cleaning, and reinstallation.

It always has been thought desirable to have optical elements of the light scattering cells designed in such a manner as to prevent the deposition of extraneous materials on their surfaces or, at the very least, design them in such a manner as to permit the cleaning of their internal surfaces with minimal effort. To this end, many structures requiring clean, particulate-free surfaces have been designated as "self-cleaning" such that once internal precipitants are detected they may be removed without need for disassembling the structures themselves. A process by which the initial formation of such contaminants may be reduced is taught, for example, by Davidson in U.S. Pat. No. 5,442,437 wherein windows, through which optical measurements are to be made, are so positioned that they extend into the flowing solution which, thereby, continuously " . . . scour said window to minimize contamination and clouding [thereof] . . . " This, of course, is an old concept that was disclosed in U.S. Pat. No. 4,616,927, referenced above, and numerous other similar implementations whereby it is necessary to clean observation windows of various types. Although such cleaning may keep the observation windows clear of particulate debris for some time, eventually sufficient particles may accrete so as to interfere with light passing through some optical surface.

Another example of a self cleaning cell is U.S. Pat. No. 4,874,243 by Perren wherein the windows are at an angle to the direction of flow which results in a " . . . self cleaning action . . . " as the flowing stream passes over them. A similar example is U.S. Pat. No. 4,330,206 of Gausmann et al. wherein is shown a measurement chamber " . . . inherently self-clearing of air or gas bubbles in liquid samples . . . [which provide] inherently efficient cleansing of the measurement chamber . . . " This is achieved by outlet means lying above the optical region guiding thereby air bubbles up and out of the fluid enclosed. The fluid flowing into the measurement channel strikes the cell window obliquely, thus cleaning it and maintaining it free of contaminants.

Berger in his U.S. Pat. No. 4,496,454 describes another example of a self-cleaning mechanism for the case of electrochchemical cells used with certain forms of liquid chromatography. His invention attacks a similar problem for electrochemical detection that faces light scattering detection: the fouling of the electrode surfaces during measurement which, in turn, affects the detector response. In the light scattering case, the optical surfaces can become fouled with particulates and small air bubbles. Berger achieves his cleaning by using a capillary tube to generate a water jet perpendicular to the detector electrode surface.

In addition to such fluid cleaning means described above, there exist a number of mechanical means exemplified by Wynn in his U.S. Pat. No. 5,185,531. In Wynn's implementation, the optical windows are kept clean by introducing periodically mechanically controlled flexible wiper blades " . . . extending from opposite sides of [a] . . . blade holder for wiping engagement with the window surfaces . . . " Other implementations of a wiping motion to clean an optical cell may be found in U.S. Pat. No. 3,844,661 by Birkett et al. or U.S. Pat. No. 4,074,217 by Yanagawa.

Although the use of ultrasonic waves appears an attractive means for removing particulates from surfaces, such as described by Neefe in his U.S. Pat. No. 4,457,880, it has never been used as a component of an optical cell to permit self cleaning action. There are three basic reasons for this omission. First is the fact that there has been neither means for establishing a proper frequency regime to achieve such cleaning nor means for localizing the cleaning action to the internal cell surfaces that require it. Secondly, even were such a self cleaning device integrated with the cell structure, there could be no assurance that, once removed from the internal cell surfaces, the particulates would not re-adhere or simply remain within the cell to adhere later to some other region. Finally, traditional ultrasonic waves used in cleaning are generated at frequencies of the order or 50 kHz, which, at the power levels traditionally employed and in fluids such as water, induce cavitation effects that result in the generation of bubbles. Such bubbles are most helpful because of their implied scrubbing action on the surfaces to be cleaned. Were such bubbles generated within an optical cell, the bubbles themselves could be expected to adhere to surfaces within the fine interstices of such cells defeating, thereby, the cleaning concept ab initio.

Ohhashi in his U.S. Pat. No. 4,672,984 extends the ultrasonic concept for cleaning optical surfaces by providing a plurality of cleaning steps, each of which may involve a different working liquid and/or ultrasonic intensity applied over varying periods of time. Once again, such cleaning is done externally to any enclosed structure with the parts to be cleaned transported individually to the array of cleaning baths. He does not discuss the frequency of the applied ultrasonic frequencies nor any possible variations thereof, so one assumes that he employ the standard cavitation prone frequencies around 50 kHz.

Honda et al. in their U.S. Pat. No. 5,656,095 introduce the concept of multiple frequencies, some of which are applied intermittently to destroy the bubbles generated by the continuously applied frequency. Such an action results in corresponding pressure pulses to which is attributed a " . . . greatly improved . . . " washing effect. They consider so-called low frequency generation as occurring at frequencies of 28 kHz, 45 kHz, and 100 kHz whereas high frequency generation describes generation at 160 kHz. The high frequency ultrasonic waves are said to generate bubbles in the size range of 20 $\mu$m to 500 $\mu$m while the intermittent low frequency waves destroy the bubbles, generating as they collapse, even higher orders of ultrasonic waves.

The present invention is concerned with the implementation of an ultrasonic cleaning device that is integrated with an optical flow cell and controlled in such a manner as to permit sonic coupling with those internal regions of the cell most needed to be particulate free. Sonic waves are used in a manner by which cavitation is avoided whenever possible since such cavitation can cause etching or other damage to finely polished optical surfaces.

SUMMARY OF THE INVENTION

This invention presents a new design concept for the cleaning of optical surfaces within flow cells used in conjunction with light scattering measurements such as commonly employed in the field of analytical chemistry and, more particularly, for liquid chromatography. Basic to this invention is the incorporation into the flow cell structure itself of means to provide internal to the flow cell extremely high frequency sonic waves such as would be produced by means of an electrically driven piezoelectric transducer. The frequencies of these waves are much greater than those employed by Honda et al. In order to avoid cavitation, yet be in resonance with the typical internal dimensions of the cleansed flow cells, frequencies of the order of 1 MHz/sec are employed. There are many different types of flow cells for which this design would be useful including those referenced above. In B. Chu's textbook on "Laser light scattering", a number of additional designs may be found; though these are by no means exhaustive.

Key to this invention are four features: 1) integrating, by good mechanical contact means, the sonic source, a piezoelectric transducer in the preferred embodiment, and the optical flow cell; 2) varying the frequency of the applied ultrasonic waves so as to couple well with those internal regions where the dislodgment of particulates is required; 3) using frequencies of the order of a MHz which are much greater than those traditionally used for ultrasonic cleaning purposes and, at practical power levels, beyond the frequencies that conventionally would cause cavitation in most liquids, and 4) providing a flowing fluid means during the application of the ultrasonic waves by which dislodged particulates may be removed from the cell.

Although such an integrated cleaning technique may be applied to static optical cells that are not generally operated in a flow through mode, when used with such mechanically coupled ultrasonic waves, means must be provided to permit a flow stream to remove particles dislodged by said sonic cleaning during the application of said ultrasonic waves.

The requirement that the frequency of the applied sonic waves must be adjustable, so as to couple the sonic energy most efficiently to the internal regions of the flow cell structure most prone to the presence of unwanted particulates, may equally well be served by automatically, and repetitively, scanning a range of frequencies that includes those best suited for the internal regions to be cleaned. Note that at frequencies of the order of 1 MHz in water, the associated wavelengths are of the order of 1.5 mm, approximately the diameter of the flow cell of the flow cell of U.S. Pat. Nos. 4,616,927 and 5,404,217 and related structures. The dislodgment of particles by the present inventive means relies upon mechanical displacement by the ultrasonic waves themselves rather than the more traditional scrubbing action created in large measure by the cavitation created air bubbles turbulently bombarding the affected surfaces.

The fluid that must be flowing through the flow cell structure during application of the ultrasonic waves throughout the structure must be in itself particle-free. When applied to a flow cell in conjunction with a chromatographic separation, this fluid would correspond to the so-called mobile phase of the chromatographic separation process. Such fluids should be free of particulates and are often degassed and filtered prior to use in the chromatograph. Additionally, since the ultrasonic field can induce particle aggregation within the flow cell, the resulting aggregates are more easily flushed from the flow cell.

DETAILED DESCRIPTION OF THE INVENTION

Figure 1:
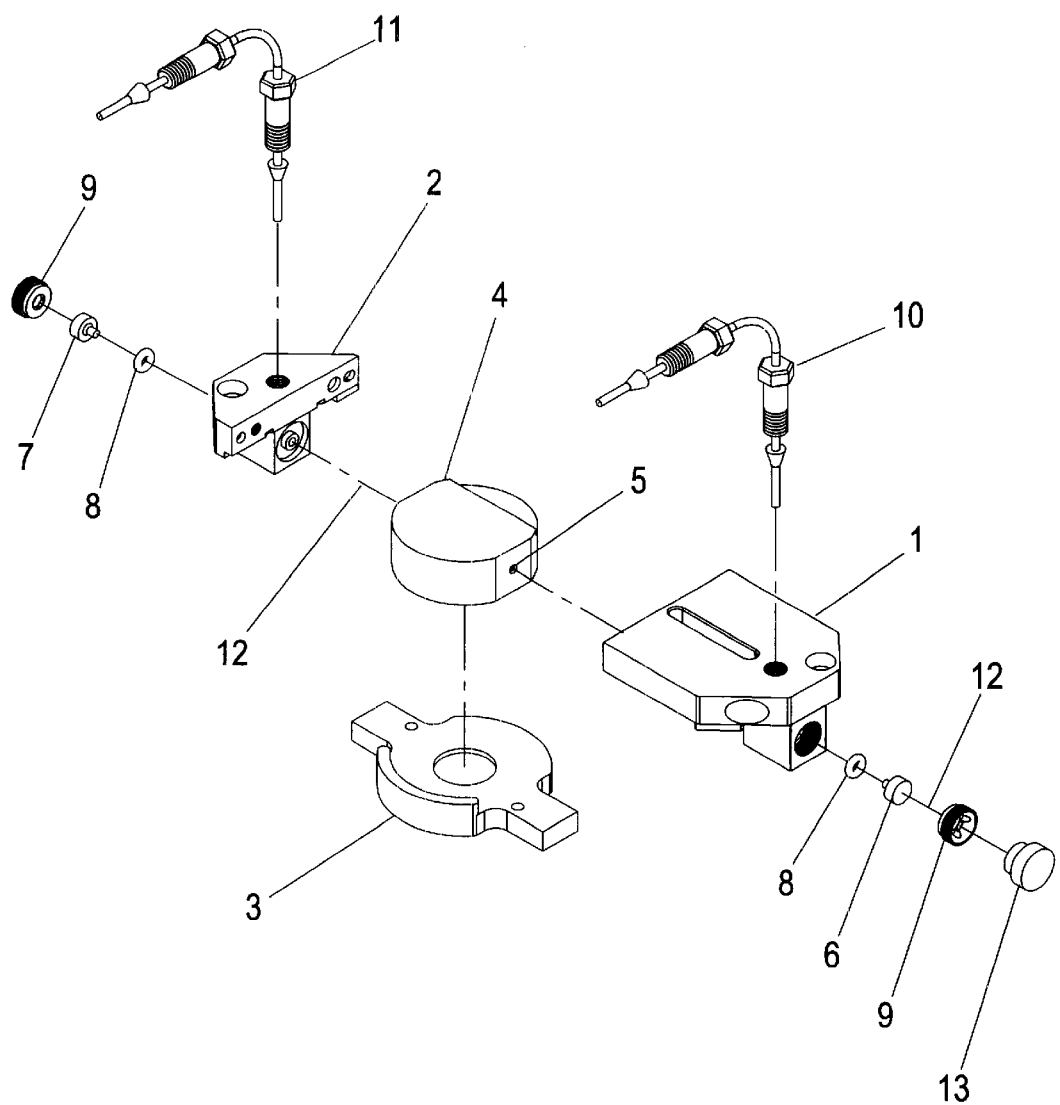
FIG. 1 is an exploded view of a flow cell similar to the type disclosed in U.S. Pat. No. 5,404,217.
Figure 2:
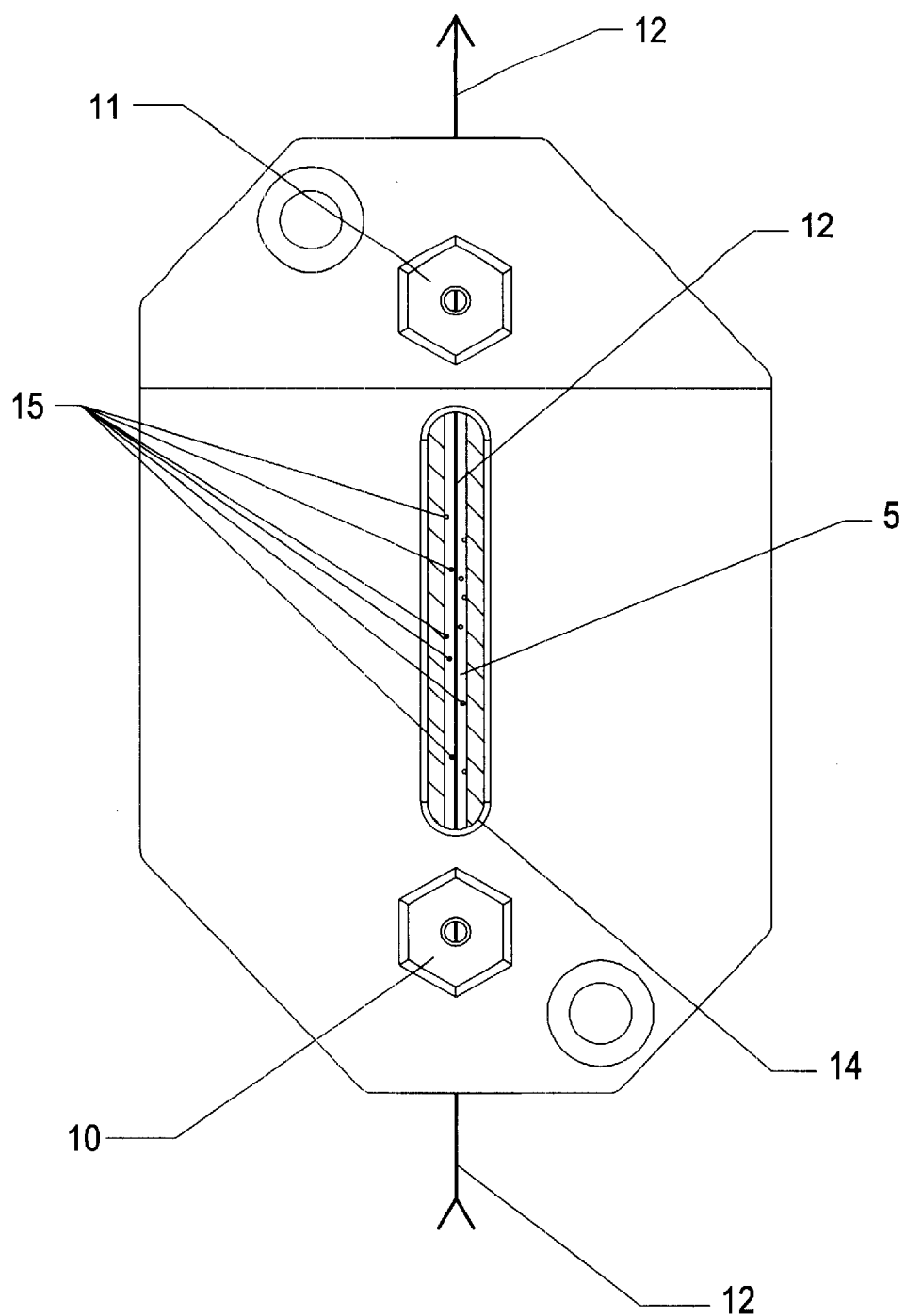
FIG. 2 shows a top view of the cell of FIG. 1 providing a port through which may be observed the illuminating laser beam and bore.

FIG. 1 shows an exploded view of the key elements of a flow cell of the type disclosed in U.S. Pat. No. 5,404,217. A manifold comprised of elements 1, 2, and 3 hold a glass cell 4 through which is a bore 5. At each manifold end is a glass window 6, 7 suitably sealed by O-ring means 8 and locking fixtures 9. Fluid, containing solvated molecules or entrained particles enters through fitting 10 and exits cell through 11. An illumination source, usually a focused beam 12 from a laser 13, enters through window 6. This figure shows a characteristic flow cell structure containing many internal surfaces and regions capable of trapping particulates or permitting precipitates to form thereon. A top view of this cell is shown in FIG. 2 providing a port 14 through which the laser beam 12 and bore 5 may be observed. In the event there are particles 15 present on the walls of the bore 5, often they may be visually observed appearing as bright sources of light. Accordingly, it is an objective of this invention to provide a means by which such extraneous light sources, arising from particulates affixed to the cell walls, may be removed from this type of flow cell as well as any other structures wherein such particulates may become affixed.

In the present specification, the term "flow cell" is used to describe a structure comprised of the glass cell itself, the windows through which the incident beam of light enters, and all supporting and ancillary elements such as the various pieces of the manifold shown in FIG. 1. Although the light source for the preferred embodiment of this invention is generally referred to as a laser, the invention applies equally well to other types of optical flow cells where their light source may be from incandescent lamps, light emitting diodes, arc lamps, etc., or even internally generated by constituents of the sample itself.

Figure 3:
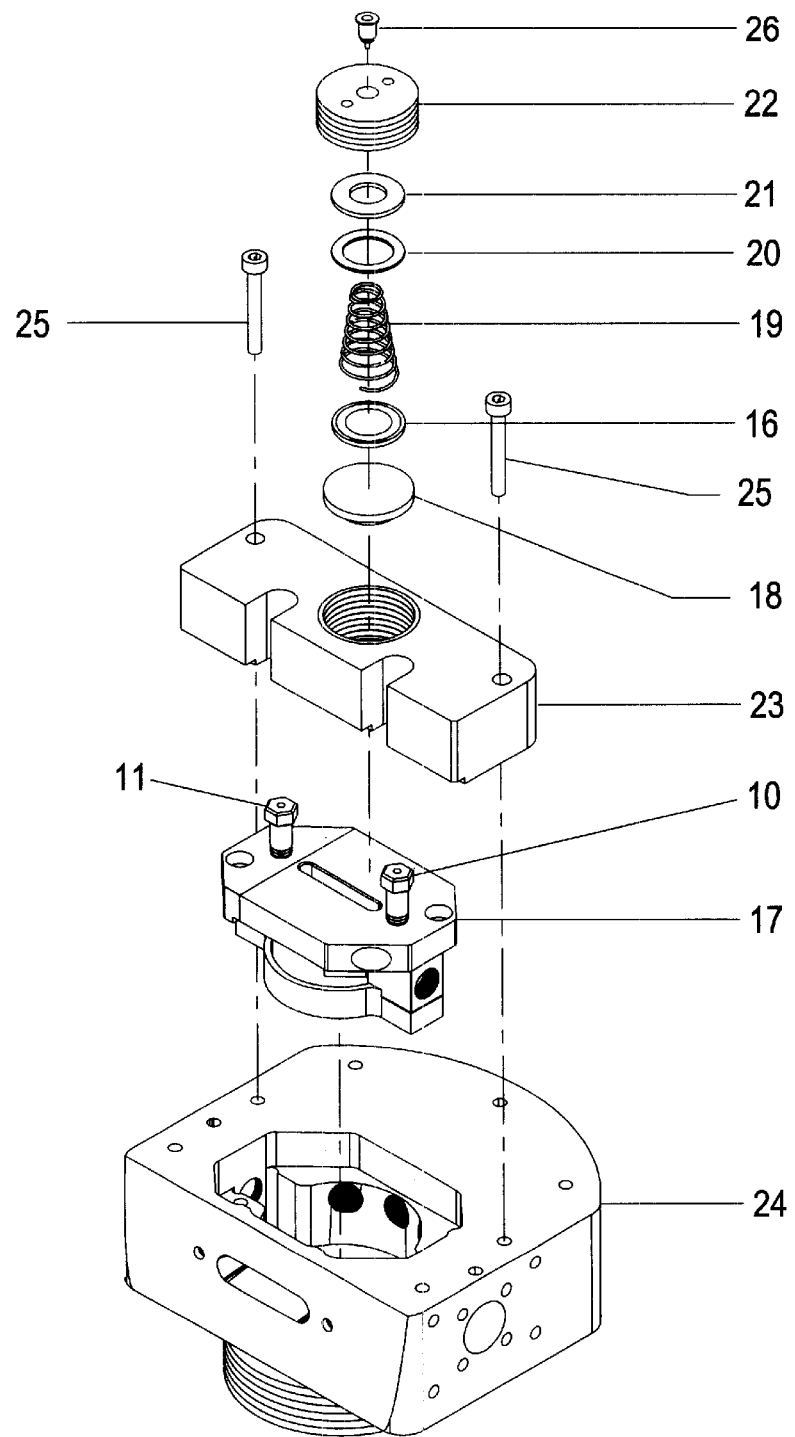
FIG. 3 shows a top view of a piezoelectric transducer coupled to a flow cell structure; which permits direct observation of particulates therein.

A preferred embodiment of the invention is shown in FIG. 3 wherein a piezoelectric transducer 16 is maintained in mechanical contact with the flow cell 17 by illustrated means as follows: direct contact plate 18 to which said piezoelectric transducer 16 is bonded, electrically conductive spring 19 compressed against said transducer by washer means 20 which distributes pressure evenly as imparted from spring washer 21, and threaded retainer 22 which hold assembly within housing module 23. The assembly housing 23 is mechanically attached to the read head 24, holding the flow cell 17, by bolt means 25. Power is supplied to said transducer via power connector means 26.

The preferred embodiment, just described, provides for firm mechanical contact with the flow cell of the contact plate 18 to which the piezoelectric transducer 16 is attached. The mechanical contact is achieved by pressure means imparted to piezoelectric transducer/contact plate via compression of the spring washer 21 and conductive spring 19 by the compression occurring as the threaded retainer 22 is threaded into the assembly housing 23. The housing 23 may include a stopping means whereby a limiting compression may be set. Alternatively, said piezoelectric transducer may be attached directly through bonding or other affixation means including gluing or cementing using epoxies or other adhesives. Obviously, there are many other locations on any given flow cell structure where such transducer device may be attached to make good mechanical contact for use subsequently to generate sonic waves permeating throughout said flow cell bore and other internal regions wherein particulates may form or become attached.

The concept of attaching a piezoelectric transducer directly to a surface for purposes of removing particulates is not new. For example, Collier in his U.S. Pat. No. 5,724,186 shows how such an attachment of two piezoelectric transducers, in a so-called bi-morph configuration, can provide a means for clearing a vehicular rear view mirror of water droplets. However, the concept of attaching an ultrasonic transducer to a structure for purposes of cleaning inaccessible internal enclosed regions is new and unique. Note that the particles of Collier's are limited to water droplets which must be in an air environment with the mirror face essentially parallel to the earth's gravitational field.

In the preferred embodiment of an electronic driving circuit for powering the ultrasonic transducer, of the type exemplified by a piezoelectric transducer, it should generate sonic waves spanning a broad swept range of frequencies. Since it is not generally possible to predict exactly the frequency that would couple best with the particular internal regions of the flow cell structure wherein affixed particles would be loosened therefrom by the corresponding sonic waves, the preferred embodiment of this invention allows for the sweeping of the excitation frequency generated by the piezoelectric transducer. Each internal region will have an associated range of frequencies best coupled for purposes of dislodging particulates. Therefore, by sweeping the frequency applied, one can insure that such optimal drive frequencies will have been applied. We have found that the swept range should be between about 0.5 MHz and 5 MHz for the structures such as shown in FIG. 1.

Although the preferred embodiment of this invention suggests that extremely high intensity ultrasonic waves be employed operating at the megahertz range so as to couple more effectively with the internal elements of the optical flow cell, this is certainly not the first time that such frequencies have been employed for cleaning purposes. The Branson Ultrasonics Corporation of Danbury, Conn., for example, offers for sale its 400 kHz MicroCoustic® device capable of cleaning " . . . irregular geometries, tight clearances and highly finished surfaces . . ." by non-cavitational means. However, there is no variation of frequency nor is the device integrated with the object to be cleaned. It is representative of the traditional immersion bath methods, though operated at a higher frequency. Again, all surfaces to be cleaned are external surfaces, though the Branson concept emphasizes the cleaning of surfaces containing very fine features. Accessibility of the ultrasonic waves to these fine features requires that these surfaces be placed within baths providing direct exposure to said ultrasonic waves. The possibility of coupling external sonic sources to a structure whose inner surfaces contained fine features to be cleared of adhered particles was never considered for possible application of the Branson ultra high frequency devices. This is because the Branson devices and similar devices manufactured by others are designed to clean by ultrasonic means a broad range of parts which do not include parts and surfaces internally situated with respect to complex structures such as optical flow cells.

The dislodgment of particles by the present inventive means relies upon the mechanical displacement by the ultrasonic pressure waves themselves rather than the more traditional scrubbing action created in large measure by the cavitation-created air bubbles turbulently bombarding the surfaces to be cleaned of particles. Cavitation induces the dissolution of gas from the fluid and this can result in bubbles, which, like any other foreign particulates present in the optical cell, are inimical to the performance of light scattering measurements where they may interfere with the scattered or incident light. Note that at frequencies of the order of 1 MHz in water, the associated ultrasonic wavelengths are of the order of 1.5 mm, approximately the diameter of the flow cell of U.S. Pat. Nos. 4,616,927 and 5,404,217 and related structures. Such waves may propagate longitudinally and throughout the flow channels producing pressure fluctuations both transverse and parallel to the optical surfaces thereon. Operating the ultrasonic piezoelectric transducers at conventional power levels and ultrasonic frequencies of the order of 50 kHz would generally result in the creation of additional gas bubbles further contaminating the flow cell and optics. However, at sufficiently low power levels for most fluids, such cavitation effects could be minimized, at the expense of cleaning efficiency.

During experiments with the inventive concept, it has been noted that although the sonic waves effectively dislodge the particulates from the optical regions within typical flow cells, these same particulates are driven to other proximate regions where they again become affixed. Particulates were seen also forming aggregates with other particles; such aggregates being caused by the impressed ultrasonic fields. This self-scavenging effect further helps collect dispersed particles as the applied flow stream more easily drives out larger particulates because of their greater cross section. In order to drive them out of the flow cell, it is essential that a particle free flow be directed through the cell during the ultrasonic dislodgment process. In this manner, the particulates are forced to progress toward the cell outlet while executing a somewhat random walk from one region of the cell surface to another. Even in the presence of such an imposed flow, particles are often observed to move against the stream and become re-affixed up stream. However, these are but statistically random motions, which are then superimposed upon the steady stream flow resulting in their eventual removal from the flow cell. The total time required to clear the cell of FIG. 1, for example, is of the order of a minute. Thus it is not necessary that the impressed sonic it cleansing action be always functioning. Its activation is, therefore, generally controlled by the operator of the light scattering apparatus on the basis of his/her observation of the light scattering signals being collected. Naturally, such periodic cleaning could be programmed to occur automatically using such light scattering signals and establishing therefrom the criteria indicative of the presence of particulate contaminants.

The imposed fluid flow through the flow cell structure during application of the ultrasonic waves throughout the structure must be in itself particle-free. When applied to a flow cell used for making light scattering measurements following chromatographic separation, this fluid would correspond to the so-called mobile phase. Such fluids should be free of particulates and are often degassed and filtered prior to use in the chromatograph.

For various types of optical cells wherein static or dynamic light scattering measurements are to be made and there is no other source of continuously flowing fluid to perform such flushing, it may necessary to attach or otherwise provide means by which such fluids may be introduced and removed from such cells in a continuous manner to carry out of said optical cells particles dislodged by the applied ultrasonic waves. This fluid itself, of course, must be free of particles and this usually requires both prefiltering and degassing.

The application of the present invention for optical cells that are used within chromatographs at elevated temperatures is a particularly important one. As has been discussed earlier, the traditional disassembly and cleaning procedures become even more time-consuming since the temperature of the chromatograph itself must often be reduced significantly to obtain access to the optical cell which is then removed and cleaned. High temperature chromatographs, and especially the columns used therein, can be damaged during temperature cycling which, therefore, must be carefully executed. The process of cleaning an internally mounted optical cell can, in such a case, require up to 24 hours to effect a removal, cleaning, and reinstallation. The incorporation of the self-cleaning structure in such high temperature chromatographs is, therefore, both desirable and essential. The preferred embodiment of the invention using a piezoelectric ultrasonic generator should be capable of operation at temperatures as high as 250° C.

A further problem that must be considered when such an implementation of the invention is employed concerns the ever-present fire dangers when organic solvents are used at both ambient and high temperatures. Since the ultrasonic circuitry requires application of voltages of the order of 100 V, there will exist the possibility of a spark-initiated discharge. Accordingly, for such cases, it is important that a vapor detector (such as manufactured by Figaro USA, Inc.) be present in close proximity to the ultrasonic transducer. The vapor detector can itself be used as a safety interlock to prevent operation of the transducer whenever such a leak poses a fire or explosion danger.

Now whereas the most preferable embodiments and applications of the self cleaning optical cell have been disclosed herein, it will be obvious to those skilled in the art of optical measurements and preparing the cells used therein that there are many obvious modifications and variations of the apparatus and method disclosed herein that may be implemented with equal effectiveness. All such modifications and variations are considered to be part of the invention.

What is claimed is:

1. A method for cleaning an optical flow cell containing optical elements through whose surfaces light must pass comprised of a) attaching an ultrasonic wave generator means in firm mechanical contact to said flow cell;
b) selecting a variable range of ultrasonic frequencies best coupled to the internal surfaces of said flow cell through which light passes and where precipitates and affixed particulates may occur;
c) driving said ultrasonic wave generator means over said range of ultrasonic frequencies selected; and
d) flowing a particulate free fluid through said flow cell during the period when said attached ultrasonic wave generator is activated to generate frequencies over the range being scanned.

2. The method of claim 1 where said ultrasonic generator is a piezoelectric transducer.

3. The method of claim 1 where said range of ultrasonic frequencies selected is between 0.5 and 5 MHz.

4. The method of claim 1 where said optical flow cell is the flow cell component of a light scattering photometer.

5. The method of claim 4 where said light scattering photometer is used in combination with a liquid chromatograph.

6. The method of claim 1 where said particulate free fluid is the mobile phase used with a liquid chromatographic separation.

7. The method of claim 1 where said firm mechanical contact is achieved by adhesive means.

8. The method of claim 7 where said adhesive means is provided by an epoxy material.

9. The method of claim 1 where said firm mechanical contact is provided by spring pressure means.

10. A self cleaning optical flow cell comprised of
a) a flow cell with all associated support and mounting elements;
b) an ultrasonic wave generator means attached in firm mechanical contact to said flow cell;
c) a means for driving said ultrasonic generator means over a selected variable range of ultrasonic frequencies;
d) means to flow through said optical flow cell a source of particulate free and bubble free fluid throughout the period in which said ultrasonic generator is activated.

11. The optical flow cell of claim 10 where said ultrasonic generator is a piezoelectric transducer.

12. The optical flow cell of claim 10 where said variable range of frequencies is between 0.5 and 5 MHz.

13. The optical flow cell of claim 10 where said optical flow cell is the flow cell component of a light scattering photometer.

14. The optical flow cell of claim 13 where said light scattering photometer is used in combination with a liquid chromatograph.

15. The optical flow cell of claim 10 where said particulate free fluid is the mobile phase used with a liquid chromatographic separation.

16. The optical flow cell of claim 10 where said firm mechanical contact is provided by spring pressure means.

17. The optical flow cell of claim 10 where said firm mechanical contact is achieved by adhesive means.

18. The optical flow cell of claim 17 where said adhesive means is provided by an epoxy material.

* * * * *